(12) United States Patent
Shelley et al.

(10) Patent No.: US 9,575,006 B1
(45) Date of Patent: Feb. 21, 2017

(54) METHOD AND COMPUTING SYSTEM FOR EVALUATING DEGRADATION OF AN AIR SEPERATION MODULE TUBESHEET

(71) Applicant: The Boeing Company, Chicago, IL (US)

(72) Inventors: Paul H. Shelley, Lakewood, WA (US); Erika Lane Carter, Seattle, WA (US); Tuan Quang Cao, Seattle, WA (US); Gregory James Werner, Puyallup, WA (US)

(73) Assignee: The Boeing Company, Chicago, IL (US)

( * ) Notice: Subject to any disclaimer, the term of this patent is extended or adjusted under 35 U.S.C. 154(b) by 808 days.

(21) Appl. No.: 13/940,021

(22) Filed: Oct. 7, 2013

(51) Int. Cl.
  *G01B 5/28* (2006.01)
  *G01B 5/30* (2006.01)
  *G01N 21/88* (2006.01)

(52) U.S. Cl.
  CPC .................... *G01N 21/88* (2013.01)

(58) Field of Classification Search
  CPC .......... F03D 9/002; F03D 1/001; F03D 1/003; F03D 1/06; F03D 7/00; F03D 7/042; F03D 80/70; C08L 75/08; G05B 2219/45031; G05B 13/04; G05B 13/042; G05B 19/418; G05B 19/4189; G05B 2219/31276
  See application file for complete search history.

(56) References Cited

U.S. PATENT DOCUMENTS

| | | | |
|---|---|---|---|
| 7,800,069 B2 | 9/2010 | Shelley et al. | |
| 7,919,753 B2 | 4/2011 | Shelley et al. | |
| 7,956,327 B2 | 6/2011 | Shelley et al. | |
| 2010/0269698 A1* | 10/2010 | Yates | B01D 53/228 96/10 |
| 2012/0145639 A1* | 6/2012 | Mallavarapu | B01D 15/00 210/683 |

* cited by examiner

*Primary Examiner* — Roy Y Yi
(74) *Attorney, Agent, or Firm* — Alston & Bird LLP

(57) ABSTRACT

A method, computing system and computer program product are provided to facilitate the inspection of an air separation module and to determine the degradation of an air separation module tubesheet. In the context of a method, an air separation module tubesheet is subjected to infrared spectroscopy by exposing the air separation module tubesheet to a spectrum of infrared radiation and collecting a spectrum of return signals. The method also includes providing a regression model based upon a multivariate regression of a representation of the infrared spectra collected from a plurality of air separation module tubesheet samples having different predefined conditions. The method further includes determining a condition of the air separation module tubesheet based upon a representation of the spectrum collected from the air separation module tubesheet and the regression model.

20 Claims, 6 Drawing Sheets

METHOD AND COMPUTING SYSTEM FOR EVALUATING DEGRADATION OF AN AIR SEPERATION MODULE TUBESHEET

TECHNOLOGICAL FIELD

An example embodiment of the present disclosure relates generally to the inspection of an air separation module tubesheet and, more particularly, to a method, computing system and computer program product for evaluating the degradation of an air separation module tubesheet.

BACKGROUND

Air separation modules are designed to separate one or more components, such as an inert gas, from air. By separating an inert gas, such as nitrogen, from air, the inert gas can be utilized for various purposes. For example, the inert gas may fill an environment that may be flammable or unstable if the environment were otherwise filled with air and subjected to a spark or other ignition source. For example, an air separation module may produce nitrogen that is utilized to fill the ullage or headspace within a fuel tank so as to reduce the possibility of an explosive event.

An air separation module generally includes a plurality of hollow fiber membranes. The opposed ends of the hollow fiber membranes may be affixed relative to one another by a tubesheet. An air separation module tubesheet may be formed of a tubesheet potting matrix that surrounds end portions of the hollow fiber membranes so as to secure the hollow fiber membranes in position and to prevent the passage of air around the hollow fiber membranes with the air, instead, being forced through the hollow fiber membranes. A hollow fiber membrane may be constructed of a material, such as polysulfone, that preferentially permits oxygen and moisture to pass through the membrane walls while maintaining the inert gas, such as nitrogen, within the hollow fiber membrane, thereby separating the inert gas enriched air from the oxygen enriched air.

The exposure of the tubesheet potting matrix of an air separation module tubesheet to air at elevated temperatures and, more particularly, to moisture and/or contamination, such as ozone, within the air may cause the matrix to be degraded. In this regard, cracks may form in the matrix over time following exposure to air with some of the air thereafter passing through the cracks in the matrix as opposed to propagating through the hollow fiber membranes. In instances in which air passes through the cracks of the air separation module tubesheet, the air separation module may perform less efficiently, such as by not cleanly separating the inert gas from the air and, in some instances, producing less inert gas in response to the receipt of the same quantity of air.

Techniques have therefore been developed to inspect air separation module tubesheets in order to determine if an air separation module tubesheet has degraded, such as by the development of cracks within the air separation module tubesheets. These inspection techniques generally require the air separation modules to be removed from service for an evaluation that is conducted by an expert. By requiring that the air separation module be taken out of service and inspected by an expert, the techniques for inspecting air separation modules are generally more costly and time-consuming than may be desired.

BRIEF SUMMARY

A method, computing system and computer program product are provided in accordance with an example embodiment of the present disclosure in order to facilitate the inspection of an air separation module and to determine the degradation of an air separation module tubesheet. In this regard, the method, computing system and computer program product may evaluate the degradation of the air separation module tubesheet in a non-destructive manner. Additionally, the method, computing system and computer program product of an example embodiment may evaluate the degradation of an air separation module tubesheet in a more efficient manner such that the air separation module may quickly return to service if the air separation module has not experienced sufficient degradation. As such, the method, computing system and computer program product may provide for the more efficient evaluation of an air separation module so as to reduce the maintenance costs and time associated therewith.

In one embodiment, a method of evaluating degradation of an air separation module tubesheet is provided that includes subjecting the air separation module tubesheet to infrared spectroscopy by exposing the air separation module tubesheet to a spectrum of infrared radiation and collecting a spectrum of return signals. The method of this embodiment also includes providing a regression model based upon a multivariate regression of a representation of the infrared spectra collected from a plurality of air separation module tubesheet samples having different predefined conditions. The method further includes determining a condition of the air separation module tubesheet based upon a representation of the spectrum collected from the air separation module tubesheet and the regression model. For example, the method may determine the condition of the air separation module tubesheet by determining a residual life of the air separation module tubesheet or a strength of a tubesheet potting matrix.

The method of one embodiment may provide the regression model by providing a regression vector. In this embodiment, the method may determine the condition of the air separation module tubesheet by determining a dot product of the regression vector and the representation of the spectrum collected from the air separation module tubesheet. In one embodiment, the method also includes providing a plurality of air separation module tubesheet samples following exposure to different predefined degradation conditions. The method of this embodiment also includes collecting infrared spectra from each of the air separation module tubesheet samples and performing multivariate regression for representations of the infrared spectra collected from each of the air separation module tubesheet samples. In this embodiment, the method may also perform data pre-processing of the infrared spectra collected from each of the air separation module tubesheet samples prior to performing the multivariate regression. In regards to performing the multivariate regression, the method of one embodiment may perform a partial lease squares multivariate regression for representations of the infrared spectra collected from each of the air separation module tubesheet samples.

In another embodiment, a computing system for evaluating degradation of an air separation module tubesheet is provided. The computing system includes a memory configured to store a regression model based upon a multivariate regression of a representation of an infrared spectra collected from a plurality of air separation module tubesheet samples having different predefined conditions. The computing system also includes processing circuitry configured to receive a spectrum of return signals collected upon subjecting the air separation module to infrared spectroscopy that exposes the air separation module tubesheet to a spectrum of infrared radiation. By way of example, the computing system of one embodiment may also include an infrared spectrometer configured to expose the air separation module tubesheet to the spectrum of infrared radiation and to collect the spectrum of return signals for analysis by the processing circuitry. The processing circuitry is also configured to determine a condition of the air separation module tubesheet based upon a representation of the spectrum collected from the air separation module tubesheet and the regression model. For example, the processing circuitry may be configured to determine the condition of the air separation module tubesheet by determining a service life of the air separation module tubesheet or a strength of a tubesheet potting matrix.

In an embodiment in which the regression model stored by the memory includes a regression vector, the processing circuitry may be configured to determine the condition of the air separation module tubesheet by determining a dot product of the regression vector and the representation of the spectra collected from the air separation module tubesheet samples. In one embodiment, the processing circuitry is further configured to receive infrared spectra from each of a plurality of air separation module tubesheet samples following exposure to different predefined degradation conditions and to perform multivariate regression for representations of the infrared spectra received from each of the air separation module tubesheet samples. The processing circuitry of this embodiment may also be configured to perform data preprocessing of the infrared spectra received from each of the air separation module tubesheets prior to performing multivariate regression. The processing circuitry of this embodiment may also be configured to perform the multivariate regression by performing a partial lease squares multivariate regression for representations of the infrared spectra collected from each of the air separation module tubesheet samples.

In a further embodiment, a computer program product is provided that includes a non-transitory computer-readable storage medium having computer-executable program code portions stored therein with the computer-executable program code portions configured, upon execution, to receive a spectrum of return signals collected upon subjecting an air separation module tubesheet to infrared spectroscopy that exposes the air separation module tubesheet to a spectrum of infrared radiation. The computer-executable program code portions are also configured to access a regression model based upon a multivariate regression of a representation of the infrared spectra collected from a plurality of separation module tubesheet samples having different predefined conditions. The computer-executable program code portions are also configured to determine a condition of the air separation module tubesheet based upon a representation of the spectrum collected from the air separation module tubesheet and the regression model. Various conditions of the air separation module tubesheet may be determined based upon the representation of the spectrum collected from the air separation module tubesheet and the regression model including a service life of the air separation module tubesheet or a strength of a tubesheet potting matrix.

In an embodiment in which the regression model includes a regression vector, the computer-executable program code portions that are configured to determine the condition of the air separation module tubesheet may include computer-executable program code portions configured to determine a dot product of the regression vector and the representation of the spectra collected from the air separation module tubesheet samples. In one embodiment, the computer-executable program code portions may be further configured to receive infrared spectra from each of a plurality of the air separation module tubesheet samples following exposure to different predefined degradation conditions and to perform multivariate regression for representations of the infrared spectra received from each of the air separation module tubesheet samples.

BRIEF DESCRIPTION OF THE SEVERAL VIEWS OF THE DRAWINGS

Figure 1:
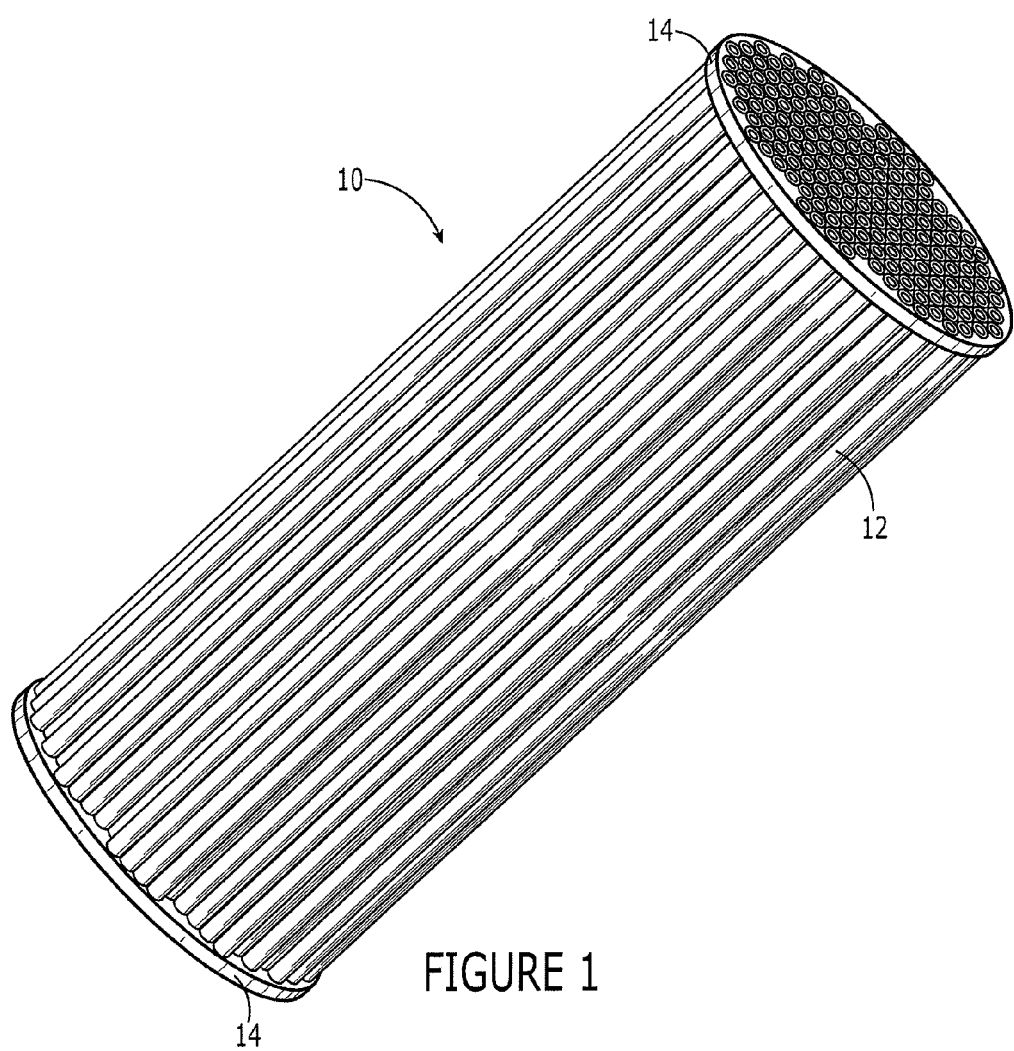
Figure 2:
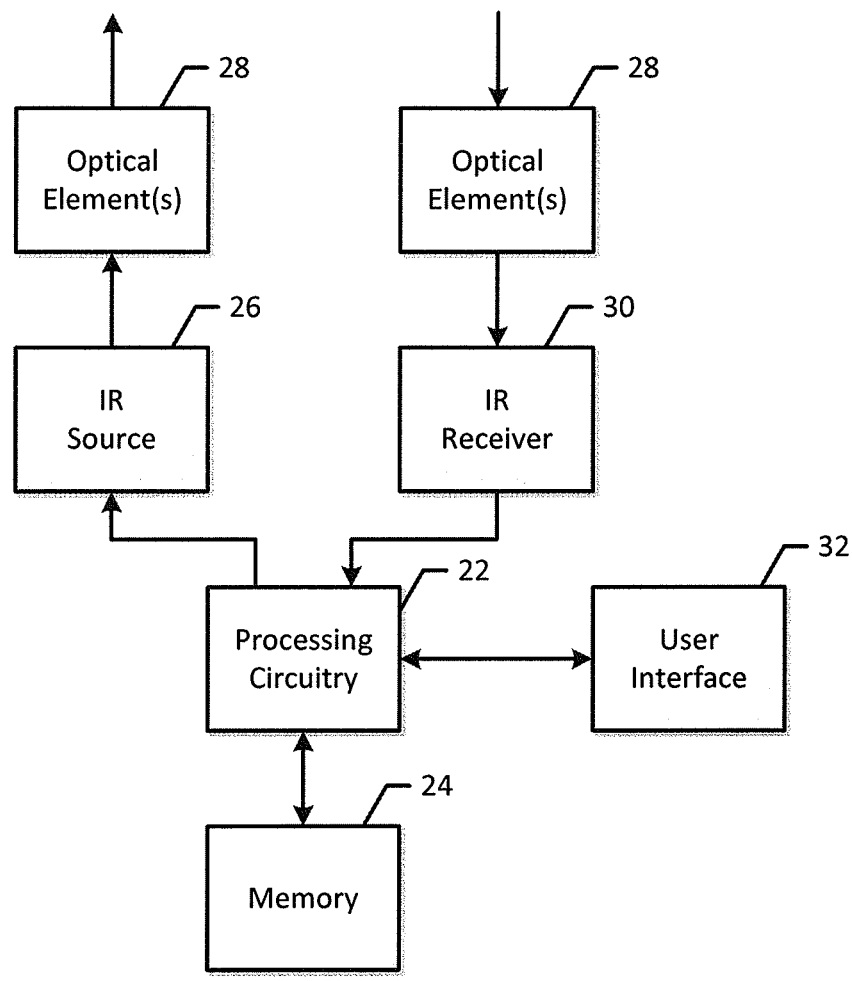
Figure 3:
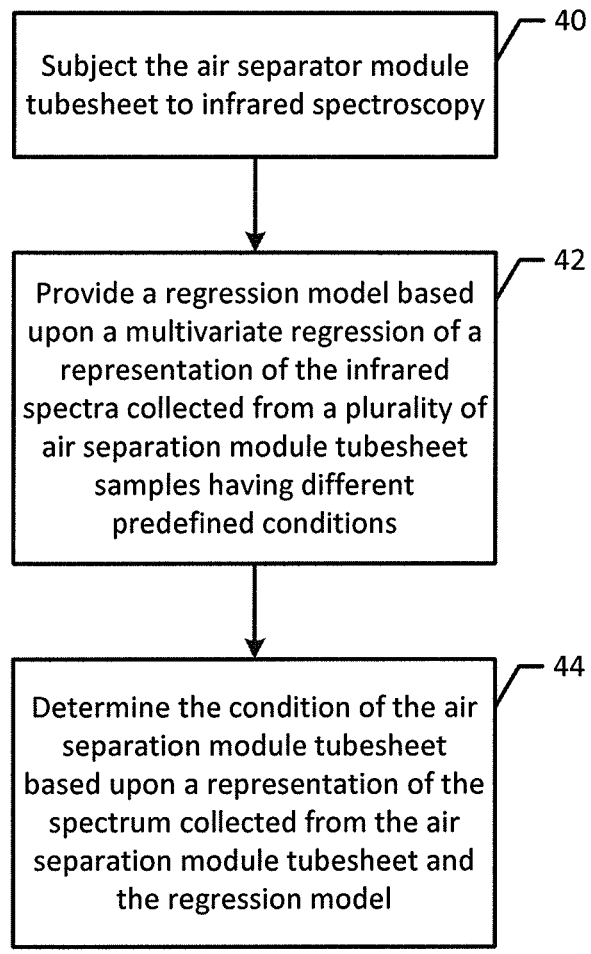
Figure 4:
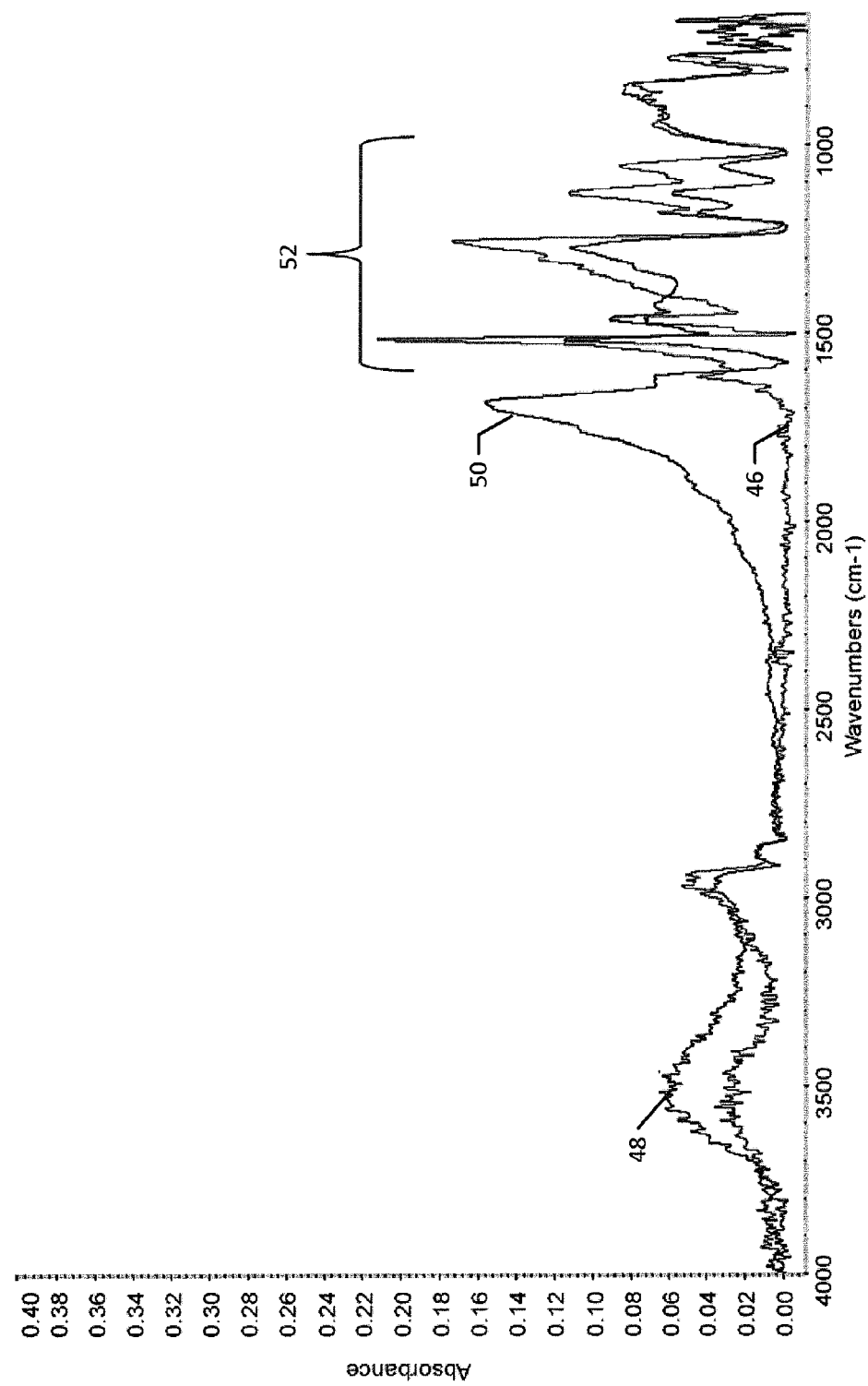
Figure 5:
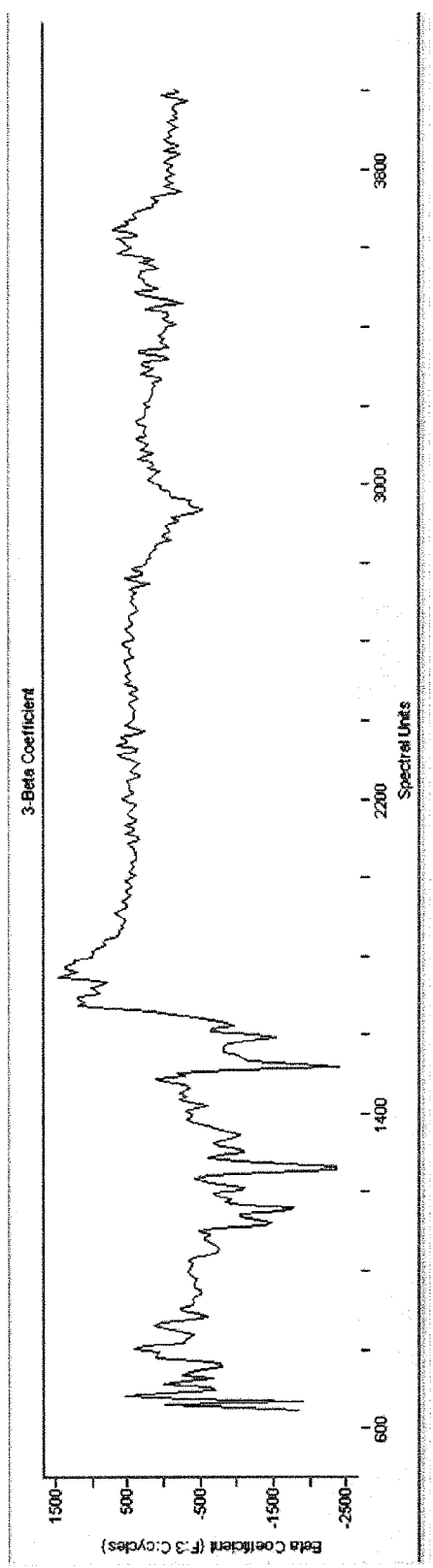
Figure 6:
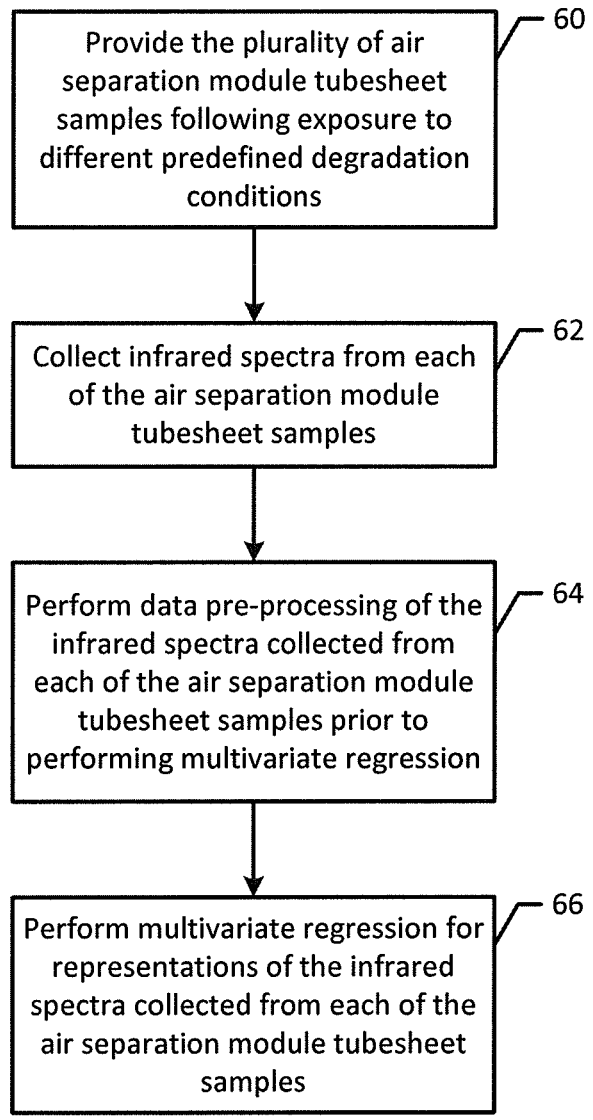

Having thus described certain embodiments of the present disclosure in general terms, reference will now be made to the accompanying drawings, which are not necessarily drawn to scale, and wherein:

FIG. 1 is a perspective view of an air separation module;

FIG. 2 is a block diagram of an infrared spectrometer including a computing system that may be specifically configured in accordance with an example embodiment of the present disclosure;

FIG. 3 is a flow chart illustrating operations performed in order to evaluate the degradation of an air separation module tubesheet in accordance with an example embodiment of the present disclosure;

FIG. 4 is a graphical representation of the absorbance of an air separation module tubesheet in response to infrared signals having different wavelengths;

FIG. 5 is a graphical representation of a regression vector that may be utilized in accordance with an example embodiment of the present disclosure in order to determine the condition of the air separation module tubesheet; and FIG. 6 is a flow chart illustrating the operations performed in order to create a regression model in accordance with an example embodiment of the present disclosure.

DETAILED DESCRIPTION

The aspects of the disclosure now will be described more fully hereinafter with reference to the accompanying drawings, in which some, but not all examples are shown. Indeed, this disclosure may be embodied in many different forms and should not be construed as limited to the examples set forth herein; rather, these examples are provided so that this disclosure will satisfy applicable legal requirements. Like numbers refer to like elements throughout.

Referring now FIG. 1, an air separation module 10 is depicted. The air separation module includes a plurality of hollow fiber membranes 12, which will be hereinafter generally referenced as tubes. The tubes may be arranged so as to extend in parallel between opposed first and second ends. The air separation module may also include an air separation module tubesheet 14 for engaging the plurality of tubes and for maintaining the relative positions of the tubes. As shown in the illustrated embodiment, an air separation module may include a plurality of tubesheets, such as first and second tubesheets proximate the first and second ends, respectively, of the tubes. Each tubesheet may be formed of a tubesheet potting matrix, such as an epoxy, a bismalimide or a polyimide, for securely engaging the tubes. Prior to any degradation, the only openings through an air separation module tubesheet are through the tubes themselves as the tubesheet prevents air from passing between the tubes or otherwise through the tubesheet.

The tubes 12 may be formed of a material that is preferentially permeable to oxygen and moisture relative to the other components of air, such as inert gas, e.g., nitrogen. Thus, air entering the tubes of an air separation module 10 may pass through the tubes towards the opposed end. During propagation through the tubes, oxygen and moisture may pass through the walls of the tubes so as to be separated from the other components of the air, such as an inert gas, e.g., nitrogen, that remains within the tubes and that continues to propagate toward the opposed end of the tubes. As such, the air that passes through the walls of the tubes may be oxygen enriched air, while the air that remains within the tubes may be an inert gas enriched air, such as nitrogen enriched air. By way of example, air received by the tubes may have 21% oxygen, 68.9% nitrogen, 0.02% moisture and 0.08% organic vapor. The nitrogen enriched air that exits from the end of the tubes may have 6% oxygen, 93.9% nitrogen, 0.001% moisture and the rest organic vapor, while the oxygen enriched air that passes through the walls of the tubes may have 35% oxygen, 64.9% nitrogen and the rest is moisture and very little of organic vapor. In one embodiment, the tubes may be formed of polysulfone with a coating that forms an air separating membrane, such as a coating of polysulfone, polyamide, poly-phenolene oxide (PPO), polyimide, etc., to provide for separation of the air components. The inert gas, such as the nitrogen enriched air, that reaches the end of the tubes of an air separation module may then be collected and utilized for various purposes, such as for filling the ullage or head space within a fuel tank.

In order to detect instances in which an air separation module tubesheet 14 has become degraded, a computing system and method are provided according to an example embodiment to expose the air separation module tubesheet to a spectrum of infrared radiation such that an analysis of the return signals permits the condition of the air separation module tubesheet to be determined. As such, the air separation module tubesheet may be inspected so as to determine the state of the matrix degradation and, thus, the strength of the matrix which may, in turn, be correlated to the likely formation of cracks or other inconsistencies due to the weakening of the matrix system that may permit air to pass through the tubesheet, as opposed to being directed solely through the tubes 12. By relying upon infrared spectroscopy, the air separation module tubesheet may be inspected in a non-destructive manner and the utilization of a portable infrared spectrometer in at least some instances may permit the air separation module 10 to be inspected in the field, thereby reducing, if not eliminating, the time that the air separation module must be removed from service to be inspected.

As shown in FIG. 2, the computing system that may be specifically configured in accordance with an example embodiment of the present disclosure may be embodied by an infrared (IR) spectrometer 20. In the illustrated embodiment, the IR spectrometer that includes the computing system may be a portable IR spectrometer. However, the IR spectrometer may be fixed or otherwise non-portable in other embodiments. Still further, the computing system may be distinct and remote from the IR spectrometer in other embodiments, although the computing system would generally be in communication with the IR spectrometer so as to control the irradiation of an air separation module tubesheet 14 and the collection and analysis of the return signals. For purposes of example, but not of limitation, however, a portable IR spectrometer including the computing system configured in accordance with an example embodiment will be hereinafter described. Although a portable IR spectrometer may have various shapes, sizes and weights, the portable IR spectrometer of one embodiment may have a weight of less than about 8 pounds and a size of less than about 1 foot by 1 foot so that it may be readily carried by a technician in the field.

The computing system and, in the illustrated embodiment, the IR spectrometer 20 may include processing circuitry 22 and one or more memory devices 24. The processing circuitry may, for example, be embodied as various means including one or more microprocessors, one or more coprocessors, one or more multi-core processors, one or more controllers, one or more computers, various other processing elements including integrated circuits such as, for example, an ASIC (application specific integrated circuit) or FPGA (field programmable gate array), or some combination thereof. Accordingly, although illustrated in FIG. 2 as a single processing circuitry, in some embodiments the computing system may include a plurality of processing circuits. In some example embodiments, the processing circuitry is configured to execute instructions stored in the memory 24 or otherwise accessible to the processing circuitry. These instructions, when executed by the processing circuitry, may cause the computing system to perform one or more of the functionalities as described herein. As such, whether configured by hardware or software methods, or by a combination thereof, the processing circuitry may comprise an entity capable of performing operations according to embodiments of the present invention while configured accordingly. Thus, for example, when the processing circuitry is embodied as an ASIC, FPGA or the like, the processing circuitry may comprise specifically configured hardware for conducting one or more operations described herein. Alternatively, as another example, when the processing circuitry is embodied as an executor of instructions, such as may be stored in the memory, the instructions may specifically configure the processing circuitry to perform one or more algorithms and operations described herein.

The memory 24 may include, for example, volatile and/or non-volatile memory. Although illustrated in FIG. 2 as a single memory, the memory may comprise a plurality of memories. The memory may comprise, for example, a hard disk, random access memory, cache memory, flash memory, an optical disc (e.g., a compact disc read only memory (CD-ROM), digital versatile disc read only memory (DVD-ROM), or the like), circuitry configured to store information, or some combination thereof. In this regard, the memory may comprise any non-transitory computer readable storage medium. The memory may be configured to store information, data, applications, instructions or the like for enabling the computing system to carry out various functions in accordance with example embodiments of the present invention. For example, in some example embodiments, the memory is configured to buffer input data for processing by the processing circuitry 22. Additionally or alternatively, in some example embodiments, the memory is configured to store program instructions for execution by the processing circuitry.

The IR spectrometer 20 may also include a source 26 of infrared radiation that may operate under control of the processing circuitry 22 such that the processing circuitry is configured to controllably adjust the wavelength of the infrared radiation generated by the source such that a spectrum of infrared radiation may be output. The IR spectrometer may also include one or more optical elements 28 for focusing or otherwise directing the infrared radiation generated by the source and for receiving return signals responsive to interaction of the infrared radiation generated by the source with an air separation module tubesheet 14. However, the optical elements are optional and need not be included in some embodiments. As shown in FIG. 2, the IR spectrometer may also include a receiver 30 for receiving the return signals. The processing circuitry may be in communication with the receiver so as to analyze the return signals as described hereinafter.

The IR spectrometer 20 is also configured to receive power, such as from a wall outlet or, in regards to a portable IR spectrometer, from one or more batteries. The IR spectrometer of one embodiment may also include a user interface 32. The user interface may be in communication with the processing circuitry 22 to receive an indication of a user input and/or to provide an audible, visual, mechanical, or other output to a user. As such, the user interface may include one or more buttons and/or soft keys, a touch screen or other input mechanisms for receiving user input. Additionally or alternatively, the user interface may include a display or other output mechanism for providing information relating to the inspection of an air separation module tubesheet 14, such as by providing an indication that the acceptability or unacceptability of an air separation module tubesheet and/or by providing an indication of the degradation of an air separation module tubesheet.

The IR spectrometer 20 may be configured to perform either fourier transform infrared (FT-IR) spectroscopy measurements. Additionally, the IR spectrometer of one embodiment may be configured to make specular-diffuse reflectance IR spectroscopic measurements. The IR spectrometer and, more particularly, the source 26 of infrared radiation may generate infrared radiation having a variety of wavelengths within the infrared spectrum. In one embodiment, however, the source of infrared radiation may generate infrared radiation having a wavelength between about 2500 nanometers and about 15,000 nanometers. Regardless of the wavelength, the IR spectrometer may be configured to irradiate an air separation module tubesheet 14 with infrared radiation delivered at a predetermined incident angle between about 30° and about 60°, such as about 45°, and to collect return signals from the air separation module tubesheet through a broad range of angles including the incident angle.

With reference to FIG. 3, the operations performed, such as by a computing system specifically configured in accordance with an example embodiment of the present disclosure, are illustrated. As shown in block 40 of FIG. 3, an air separation module tubesheet 14 may be evaluated to detect degradation by subjecting the air separation module tubesheet to infrared spectroscopy. In this regard, the air separation module tubesheet may be exposed to a spectrum of infrared radiation and a spectrum of return signals, responsive to interaction of the infrared radiation with the air separation module tubesheet, may be collected. For example, the processing circuitry 22 may direct the source 26 of infrared radiation to output the spectrum of infrared radiation and the spectrum of return signals may then be collected by the receiver 30 for analysis by the processing circuitry.

As shown in block 42, a regression model may be provided. For example, the regression model may be stored by the memory 24 or otherwise accessible by the processing circuitry 22. As described below in conjunction with FIG. 6, the regression model may be based upon a multivariate regression of a representation of the infrared spectra collected from a plurality of air separation module tubesheet samples having different predefined conditions that span the range of possible conditions for an air separation module tubesheet. For example, the plurality of air separation module tubesheet samples may have different lengths of service life and/or may exhibit different degrees or levels of strength of the tubesheet potting matrix that forms the air separation module tubesheet 14.

As shown in FIG. 4, the return signals that are captured by the receiver 30 in response to the irradiation of an air separation module tubesheet 14 with a spectrum of infrared radiation may have different levels of absorbance for signals having different wavelengths. As an air separation module tubesheet becomes increasingly degraded, the absorbance of the air separation module tubesheet changes relative to the absorbance of the same air separation module tubesheet that has not yet experienced any degradation. With respect to FIG. 4, for example, the graphical representation depicted by the line 46 illustrates the absorbance characteristics as a function of wavelength of an air separation module tubesheet having no degradation and the graphical representation depicted by the line 48 illustrates a relatively degraded air separation module tubesheet. The variations between the absorbance of a degraded air separation module tubesheet and a non-degraded air separation module tubesheet include a region designated 50 in which the absorbance of the degraded air separation module tubesheet is greater as a result of the oxidation of the tubesheet potting matrix of the degraded air separation module tubesheet. Additionally, region 52 designates a range of wavelengths in which the absorbance of the degraded air separation module tubesheet is generally diminished relative to the absorbance of a non-degraded air separation module tubesheet as a result of the different levels of degradation.

In one embodiment, the regression model may be represented by a regression vector. The regression vector may be determined in the manner described below in conjunction with FIG. 6. However, the regression vector may be represented graphically, such as shown, for example, in FIG. 5 in which a beta coefficient in arbitrary units is graphically represented as a function of spectral units, e.g., wavenumbers, for a respective air separation module tubesheet 14. In this embodiment, the processing circuitry 22 may be configured to determine the condition of the air separation module tubesheet by determining a dot product of the regression vector, such as shown in FIG. 5, and a representation of the spectrum reflected from the air separation module tubesheet, such as the spectrum of the return signals. The result of applying the dot product may provide the condition of the air separation module tubesheet in terms that are defined by the regression vector. For example, the regression vector may be defined in terms of the service life of the air separation module tubesheet or the adhesion between the tubesheet potting matrix and the plurality of tubes 12 of the air separation module tubesheet. Thus, the result of the dot product may determine the condition of the air separation module tubesheet such that a determination may be made as to whether the air separation module tubesheet may remain in service, such as in an instance in which the air separation module tubesheet is determined to not be degraded or to have only minimal degradation less than a predetermined acceptable threshold, e.g., a service life of greater than a predefined threshold or a strength of the matrix being at least as great as a predefined threshold, or may be in need of replacement, either immediately or during the next scheduled maintenance period based upon the level of degradation of the air separation module tubesheet.

The computing system, such as the processing circuitry 22 and/or the user interface 32, may be configured to provide an indication as to the condition of the tubesheet 14. For example, the processing circuitry may cause a message to be displayed via the user interface indicating the condition of the tubesheet, such as by indication whether the tubesheet can remain in service. In an instance in which the air separation module tubesheet is to be replaced, the processing circuitry may be configured to cause a message to be displayed via the user interface indication whether the air separation module tubesheet should be replaced immediately or during the next scheduled maintenance period based upon the level of degradation of the air separation module tubesheet.

The regression model including, for example, the regression vector, may be defined in various manners including, for example, provision of the regression model by a database. In one embodiment, however, the computing system and method may determine the regression model based upon the analysis of a plurality of air separation module tubesheet samples that have been exposed to different predefined degradation conditions. As shown in block 60 of FIG. 6, a plurality of air separation module tubesheet samples may be provided following exposure of the air separation module tubesheet samples to different predefined degradation conditions. For example, the air separation module tubesheet samples may have different service lives and/or may exhibit different levels of strength of the tubesheet potting matrix (with the strength of the matrix varying inversely to the extent of degradation, that is, the strength of the matrix decreases as the degradation of the matrix increases). In one embodiment, the air separation module tubesheet samples may be selected so as to span the entire range of potential degradation conditions.

As shown in block 62, at least one and, in one embodiment, a plurality, e.g., 5, of infrared spectra are collected from each of the air separation module tubesheet samples. In this regard, each air separation module tubesheet sample may be irradiated with a spectrum of infrared radiation and the spectrum of return signals may be collected in the manner described above. As noted above, this process of irradiating an air separation module tubesheet sample with a spectrum of infrared radiation and collecting the spectrum of return signals may be performed one or a plurality of times, such as 5 times in accordance with one embodiment, and the plurality of spectra may be combined, such as by averaging.

In one embodiment, the infrared spectra collected from each of the air separation module tubesheet samples may be subjected to data pre-processing by the processing circuitry 22. See block 64. Various types of data pre-processing may be performed including, for example, one or more of smoothing, normalization, first and second derivatives of the IR spectra and peak enhancement methods.

Thereafter, the processing circuitry may perform multivariate regression for representations of the infrared spectra collected from each of the air separation module tubesheet samples in order to define the regression model that will thereinafter be utilized to characterize air separation module tubesheets 14 of an otherwise unknown condition. See block 66. In an embodiment in which the infrared spectra collected from each of the air separation module tubesheet samples has been subjected to data pre-processing, the representations of the infrared spectra collected from each of the air separation module tubesheet samples may be the resulting representation of the infrared spectra collected from each of the air separation module tubesheet samples following the data pre-processing. Multivariate regression and other multivariate statistical approaches may be used to correlate the statistically determined changes in a plurality of first variables, e.g., absorbance at various IR wavelengths, with one or more second variables, such as degradation on an air separation module tubesheet as evidenced by chemical and/ or physical changes. Various types of multivariate regression may be performed including various quantification methodologies, such as principal component regression, linear regression, multiple linear regression, stepwise linear regression, ridge regression, radial basis functions and the like. In one embodiment, however, the processing circuitry may be configured to perform a partial least squares multivariate regression for representations of the infrared spectra collected from each of the air separation module tubesheet samples. In one embodiment, the regression model may then be validated by inspecting one or more additional air separation module tubesheet samples of a known condition, such as a known service life, and determining the condition of the additional air separation module tubesheet samples utilizing the regression model.

Based upon the regression model that has been established by the analysis of a plurality of air separation module tubesheet samples that represent different predefined degradation conditions, the computing system and method of one embodiment may determine the condition of an air separation module tubesheet 14 by comparison to the air separation module tubesheet samples having different predefined degradation conditions as represented by the regression model. By utilizing IR spectroscopy, the method, computing system and computer program product of an example embodiment may evaluate the degradation of the air separation module tubesheet in accordance with a regression model in a nondestructive manner. Additionally, the method, computing system and computer program product may efficiently evaluate the degradation of an air separation module tubesheet, such as in the field, such that the air separation module may quickly return to service if the air separation module has not experienced sufficient degradation, thereby potentially reducing the maintenance costs and the time associated therewith.

As described above, FIGS. 3 and 6 illustrate flowcharts of a system, method, and computer program product according to example embodiments of the invention. It will be understood that each block of the flowchart, and combinations of blocks in the flowchart, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices 24 and executed by a processing circuitry 22 in the computing systems. As such, the computer program instructions, upon execution, may cause the processing circuitry to receive a spectrum of return signals collected upon subjecting an air separation module tubesheet 14 to IR spectroscopy, access a regression model, such as may be stored by the memory device, and determine a condition of the air separation module tubesheet, such as the service life of the air separation module tubesheet and/or the strength of a tubesheet potting matrix, by, for example, determining the dot product of a regression vector defined by the regression model and a representation of the spectra collected from the air separation module tubesheet samples. In the context of the operations depicted in FIG. 6, the computer program instructions, upon execution, may also cause the processing circuitry to receive infrared spectra from each of the plurality of air separation module tubesheet samples following exposure to different predefined degradation conditions and to perform multivariate regression for representations of the infrared spectra received from each of the air separation module tubesheet samples.

As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowchart support combinations of means for performing the specified functions and combinations of steps for performing the specified functions. It will also be understood that one or more blocks of the flowchart, and combinations of blocks in the flowchart, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, suitably configured processing circuitry 22 may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications of the various aspects of the disclosure set forth herein will become apparent to one skilled in the art to which this disclosure pertains, having the benefit of the teachings presented in the foregoing description and the associated drawings. Therefore, it is to be understood that the disclosure is not to be limited to the specific examples presented herein and that modifications and other embodiments are intended to be included within the scope of the appended claims. Although specific terms are employed herein, they are used in a generic and descriptive sense only and not for purposes of limitation.

That which is claimed:

1. A method of evaluating degradation of an air separation module tubesheet, the method comprising:
    subjecting the air separation module tubesheet to infrared spectroscopy by exposing the air separation module tubesheet to a spectrum of infrared radiation and collecting a spectrum of return signals;
    providing a regression model based upon a multivariate regression of a representation of the infrared spectra collected from a plurality of air separation module tubesheet samples having different predefined conditions; and
    determining a condition of the air separation module tubesheet based upon a representation of the spectrum collected from the air separation module tubesheet and the regression model.

2. A method according to claim 1 wherein determining the condition of the air separation module tubesheet comprises determining a service life of the air separation module tubesheet.

3. A method according to claim 1 wherein determining the condition of the air separation module tubesheet comprises determining a strength of a tubesheet potting matrix.

4. A method according to claim 1 wherein providing the regression model comprises providing a regression vector, and wherein determining the condition of the air separation module tubesheet comprises determining a dot product of the regression vector and the representation of the spectrum collected from the air separation module tubesheet.

5. A method according to claim 1 further comprising:
    providing the plurality of air separation module tubesheet samples following exposure to different predefined degradation conditions;
    collecting infrared spectra from each of the air separation module tubesheet samples; and
    performing multivariate regression for representations of the infrared spectra collected from each of the air separation module tubesheet samples.

6. A method according to claim 5 further comprising performing data pre-processing of the infrared spectra collected from each of the air separation module tubesheet samples prior to performing multivariate regression.

7. A method according to claim 5 wherein performing the multivariate regression comprises performing a partial least squares multivariate regression for representations of the infrared spectra collected from each of the air separation module tubesheet samples.

8. A computing system for evaluating degradation of an air separation module tubesheet, the computing system comprising:
    a memory configured to store a regression model based upon a multivariate regression of a representation of an infrared spectra collected from a plurality of air separation module tubesheet samples having different predefined conditions; and
    processing circuitry configured to receive a spectrum of return signals collected upon subjecting the air separation module tubesheet to infrared spectroscopy that exposes the air separation module tubesheet to a spectrum of infrared radiation, wherein the processing circuitry also configured to determine a condition of the air separation module tubesheet based upon a representation of the spectrum collected from the air separation module tubesheet and the regression model.

9. A computing system according to claim 8 further comprising an infrared spectrometer configured to expose the air separation module tubesheet to the spectrum of infrared radiation and to collect the spectrum of return signals.

10. A computing system according to claim 8 wherein the processing circuitry is configured to determine the condition of the air separation module tubesheet by determining a service life of the air separation module tubesheet.

11. A computing system according to claim 8 wherein the processing circuitry is configured to determine the condition of the air separation module tubesheet by determining a strength of a tubesheet potting matrix.

12. A computing system according to claim 8 wherein the regression model stored by the memory comprises a regression vector, and wherein the processing circuitry is configured to determine the condition of the air separation module tubesheet by determining a dot product of the regression vector and the representation of the spectrum collected from the air separation module tubesheet.

13. A computing system according to claim 8 wherein the processing circuitry is further configured to:
 receive infrared spectra from each of the plurality of air separation module tubesheet samples following exposure to different predefined degradation conditions; and
 perform multivariate regression for representations of the infrared spectra received from each of the air separation module tubesheet samples.

14. A computing system according to claim 13 wherein the processing circuitry is further configured to perform data pre-processing of the infrared spectra received from each of the air separation module tubesheet samples prior to performing multivariate regression.

15. A computing system according to claim 13 wherein the processing circuitry is configured to perform the multivariate regression by performing a partial least squares multivariate regression for representations of the infrared spectra collected from each of the air separation module tubesheet samples.

16. A computer program product comprising a non-transitory computer-readable storage medium having computer-executable program code portions stored therein, the computer-executable program code portions configured, upon execution, to:
 receive a spectrum of return signals collected upon subjecting an air separation module tubesheet to infrared spectroscopy that exposes the air separation module tubesheet to a spectrum of infrared radiation;
 access a regression model based upon a multivariate regression of a representation of the infrared spectra collected from a plurality of air separation module tubesheet samples having different predefined conditions; and
 determine a condition of the air separation module tubesheet based upon a representation of the spectrum collected from the air separation module tubesheet and the regression model.

17. A computer program product according to claim 16 wherein the computer-executable program code portions configured to determine the condition of the air separation module tubesheet comprise computer-executable program code portions configured to determine a service life of the air separation module tubesheet.

18. A computer program product according to claim 16 wherein the computer-executable program code portions configured to determine the condition of the air separation module tubesheet comprise the computer-executable program code portions configured to determine a strength of a tubesheet potting matrix.

19. A computer program product according to claim 16 wherein the regression model comprises a regression vector, and wherein the computer-executable program code portions configured to determine the condition of the air separation module tubesheet comprise computer-executable program code portions configured to determine a dot product of the regression vector and the representation of the spectrum collected from the air separation module tubesheet.

20. A computer program product according to claim 16 wherein the computer-executable program code portions are further configured to:
 receive infrared spectra from each of the plurality of air separation module tubesheet samples following exposure to different predefined degradation conditions; and
 perform multivariate regression for representations of the infrared spectra received from each of the air separation module tubesheet samples.

\* \* \* \* \*

UNITED STATES PATENT AND TRADEMARK OFFICE
CERTIFICATE OF CORRECTION

| | | |
|---|---|---|
| PATENT NO. | : 9,575,006 B1 | |
| APPLICATION NO. | : 13/940021 | |
| DATED | : February 21, 2017 | |
| INVENTOR(S) | : Shelley et al. | |

It is certified that error appears in the above-identified patent and that said Letters Patent is hereby corrected as shown below:

On the Title Page

<u>Item (54) and in the Specification, Column 1, Lines 1-3,</u>
In the title, "Method And Computing System For Evaluating Degradation Of An Air Seperation Module Tubesheet" should read --Method And Computing System For Evaluating Degradation Of An Air Separation Module Tubesheet--.

Signed and Sealed this
Sixteenth Day of May, 2017

Michelle K. Lee
*Director of the United States Patent and Trademark Office*